United States Patent
Baldi et al.

(10) Patent No.: US 9,388,239 B2
(45) Date of Patent: Jul. 12, 2016

(54) ANTI-HUMAN VEGF ANTIBODIES WITH UNUSUALLY STRONG BINDING AFFINITY TO HUMAN VEGF-A AND CROSS REACTIVITY TO HUMAN VEGF-B

(71) Applicants: Alberto Baldi, Ciudad Autonoma de Buenos Aires (AR); Adrián Daniel Góngora, Ciudad Autonoma de Buenos Aires (AR); Alejandro Gustavo Mladovan, Ciudad Autonoma de Buenos Aires (AR)

(72) Inventors: Alberto Baldi, Ciudad Autonoma de Buenos Aires (AR); Adrián Daniel Góngora, Ciudad Autonoma de Buenos Aires (AR); Alejandro Gustavo Mladovan, Ciudad Autonoma de Buenos Aires (AR)

(73) Assignees: Consejo Nacional De Investigation Cientifica, Cuidad Autonoma de Buenos Aires (AR); LABORATORIO Pablo Cassana SRL, Ciudad Autoonoma de Buenos Aries (AR)

( * ) Notice: Subject to any disclaimer, the term of this patent is extended or adjusted under 35 U.S.C. 154(b) by 0 days.

(21) Appl. No.: 14/267,504

(22) Filed: May 1, 2014

(65) Prior Publication Data
US 2015/0315270 A1 Nov. 5, 2015

(51) Int. Cl.
| | |
|---|---|
| A61K 39/395 | (2006.01) |
| C07K 16/22 | (2006.01) |
| A61K 31/7068 | (2006.01) |
| A61K 31/4745 | (2006.01) |
| A61K 31/513 | (2006.01) |
| A61K 31/519 | (2006.01) |
| A61K 31/555 | (2006.01) |
| A61K 39/00 | (2006.01) |

(52) U.S. Cl.
CPC ............ *C07K 16/22* (2013.01); *A61K 31/4745* (2013.01); *A61K 31/513* (2013.01); *A61K 31/519* (2013.01); *A61K 31/555* (2013.01); *A61K 31/7068* (2013.01); *A61K 39/3955* (2013.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,492,537 A | 1/1985 | Awerkamp |
| 4,766,106 A | 8/1988 | Katre et al. |
| 4,816,567 A | 3/1989 | Cabilly et al. |
| 4,917,888 A | 4/1990 | Katre et al. |
| 5,196,446 A | 3/1993 | Levitzki et al. |
| 5,595,898 A | 1/1997 | Robinson et al. |
| 5,616,582 A | 4/1997 | Barker |
| 5,646,153 A | 7/1997 | Spada et al. |
| 5,656,655 A | 8/1997 | Spada et al. |
| 5,679,683 A | 10/1997 | Bridges et al. |
| 5,762,923 A | 6/1998 | Gross et al. |
| 5,766,582 A | 6/1998 | Yuen et al. |
| 5,766,886 A | 6/1998 | Studnicka et al. |
| 6,005,079 A | 12/1999 | Casterman et al. |
| 6,217,866 B1 | 4/2001 | Schlessinger et al. |
| 7,192,737 B2 | 3/2007 | Horwitz |
| 7,208,582 B2 | 4/2007 | Rosen |
| 8,034,905 B2 | 10/2011 | Kavlie et al. |
| 2003/0175274 A1 | 9/2003 | Rosen |
| 2004/0209878 A1 | 10/2004 | Guzi et al. |
| 2006/0121604 A1 | 6/2006 | Handa et al. |
| 2007/0128111 A1 | 6/2007 | Reilly et al. |
| 2007/0160608 A1 | 7/2007 | Fyfe et al. |

FOREIGN PATENT DOCUMENTS

| | | |
|---|---|---|
| EP | 0236987 | 9/1987 |
| EP | 0404097 | 12/1990 |
| EP | 0593868 | 4/1994 |
| WO | WO9311161 | 6/1993 |
| WO | WO9404678 | 3/1994 |
| WO | WO9425591 | 11/1994 |
| WO | WO9513090 | 5/1995 |
| WO | WO9935146 | 7/1999 |
| WO | WO0071129 | 11/2000 |
| WO | WO0129025 | 4/2001 |
| WO | WO0232861 | 4/2002 |
| WO | WO03088900 | 10/2003 |
| WO | WO2004000105 | 12/2003 |
| WO | WO2004009542 | 1/2004 |
| WO | WO2004009601 | 1/2004 |
| WO | WO2004013145 | 2/2004 |
| WO | WO2004033693 | 4/2004 |

OTHER PUBLICATIONS

Doctoral Thesis by Adrian Daniel Gongora, 2010.*
Albini A, Tosetti F, Li VW, Noonan DM, Li WW. Cancer prevention by targeting angiogenesis. Nat Rev Clin Oncol. doi: 10.1038/nrclinonc.2012.120.

(Continued)

Primary Examiner — Christine J Saoud
(74) Attorney, Agent, or Firm — Defillo & Associates, Inc.; Evelyn A. Defillo

(57) ABSTRACT

Murine and humanized anti-human VEGF antibodies and uses are disclosed. The anti-human VEGF antibodies of the invention have higher binding affinity for human VEGF-A, are stronger inhibitors of the VEGF-A induced proliferation of endothelial cells in culture as compared with anti-human VEGF antibodies in the art. Moreover, these antibodies cross react with human VEGF-B. The antibodies of the invention inhibit tumor growth in vivo in greater extent than Bevacizumab when administered at the same dosage.

18 Claims, 5 Drawing Sheets

(56) References Cited

OTHER PUBLICATIONS

Al-Lazikani, B., et al., "Standard Conformations for the Canonical Structures of Immunoglobulins," J. Mol. Biol. 273:927-948 (1997).
Lippow MS, K, Wittrup D, Tidor B. Computational design of antibody affinity improvement beyond in vivo maturation. Nat Biotechnol.25: 1171-1176 (2007). Michels, S., et al., "Ranibizumab Therapy for Neovascular Age-Related Macular Degeneration," Retinal Physician 1:16-22 (2004).
Barbas CF 3rd, Kang AS, Lerner RA, Benkovic SJ. Assembly of combinatorial antibody libraries on phage surfaces: the gene III site. Proc Natl Acad Sci U S A. 88:7978-82 (1991).
Beckman RA, Weiner LM, Davis HM. Antibody constructs in cancer therapy: protein engineering strategies to improve exposure in solid tumors. Cancer. 109:170-179 (2007).
Morrison SL, Johnson MJ, Herzenberg LA, Oi VT. Chimeric human antibody molecules: mouse antigen-binding domains with human constant region domains. Proc Nati Acad Sci U S A. 81:6851-5 (1984).
Canavese M, Altruda F, Ruzicka T. et al. Vascular endothelial growth factor (VEGF) in the pathogenesis of psoriasis—A possible target for novel therapies? J Dermatol Sci. 58:171-176 (2010).
Pichinuk E, Benhar I, Jacobi O, Michael Chalik M, Lotem Weiss L, Ziv R, Sympson C, Karwa A, Smorodinsky NI, Rubinstein DB, Wreschner DH. Antibody Targeting of Cell-Bound MUC1 SEA Domain Kills Tumor Cells. Cancer Res. 72:3324-3336 (2012).
Chothia, C., "Domain Association in Immunoglobulin Molecules: The Packing of Variable Domains," J. Mol. Biol. 186:651-663 (1985).
Presta, L. G., et al., "Humanization of an Anti-Vascular Endothelial Growth Factor Monoclonal Antibody for the Therapy of Solid Tumors and Other Disorders," Cancer Res. 57:4593-4599 (1997).
Chothia, C., et al., "Conformations of Immunoglobulin Hypervariable Regions," Nature 342:877-883 (1989).
Rathanaswami P, Roalstad S, Roskos L, Su QJ, Lackie S, Babcook J. Demonstration of an in vivo generated sub-picomolar affinity fully human monoclonal antibody to interleukin-8. BBRC 334:1004-1013 (2005).
Crawford TN, Alfaro DV 3rd, Kerrison JB, Jablon EP. Diabetic retinopathy and angiogenesis. Curr Diabetes Rev. 5:8-13 (2009).
Sastry L, Alting-Mees M, Huse WD, Short JM, Sorge JA, Hay BN, Janda KD, Benkovic SJ, Lerner RA. Cloning of the immunological repertoire in Escherichia coli for generation of monoclonal catalytic antibodies: construction of a heavy chain variable region-specific cDNA library. Proc Natl Acad Sci U S A. 86:5728-32 (1989).
de Haard HJ, van Neer N, Reurs A, Hufton SE, Roovers RC, Henderikx P, de Bruine AP, Arends JW, Hoogenboom. HR. A large non-immunized human Fab fragment phage library that permits rapid isolation and kinetic analysis of high affinity antibodies. JBC. 274: 18218-18230 (1999).
Tan P, Mitchell DA, Buss TN, Holmes MA, Anasetti C, Foote J. "Superhumanized" antibodies: reduction of immunogenic potential by complementarity-determining region grafting with human germline sequences: application to an anti-CD28. J Immunol. 169:1119-25 (2002).
Ferrara N. Molecular and biological properties of vascular endothelial growth factor. J Mol Med. 77:527-543 (1999).

Ferrara, N. Vascular endothelial growth factor: basic science and clinical progress. Endocr. Rev. 25:581-611 (2004).
Ferrara, N., et al., "Discovery and Development of Bevacizumab, An Anti-VEGF Antibody for Treating Cancer," Nat. Rev. Drug Discov. 3:391-400 (2004).
Thurber GM, Zajic SC, Wittrup KD. Theoretic criteria for antibody penetration into solid tumors and micrometastases. J Nucl Med. 48:995-999 (2007).
Rudnick SI, Adams GP. Affinity and Avidity in Antibody-Based Tumor Targeting. Cancer Biother Radiopharm. 24: 155-161(2009).
Zhang F, Tang Z, Hou X, Lennartsson J, Li Y, Koch AW, Scotney P, Lee C, Arjunan P, Dong L, Kumar A, Rissanen TT, Wang B, Nagai N, Fons P, Fariss R, Zhang Y, Wawrousek E, Tansey G, Raber J, Fong GH, Ding H, Greenberg, DA, Becker, KG, Herbert JM, Nash A, Yla-Hertuala S, Cao Y, Watts RJ, LiX. VEGF-B is despensabel for blood vessel growth but critical for their survival, and VEGF-B targeting inhibits pathological angiogenesis. 2009. Proc. Natl. Acad. Sci. U.S.A. 106: 6152-6157 (2009).
Zhao Q, Feng Y, Zhu Z, Dimitrov DS. Human monoclonal antibody fragments binding to insulin-like growth factors I and II with picomolar affinity.Mol Cancer Ther. 10:1677-85 (2011).
Zhou Y, Goenaga AL, Harms BD, Zou H, Lou J, Conrad F, Adams GP, Schoeberl B, Nielsen UB, Marks JD. Impact of Intrinsic Affinity on Functional Binding and Biological Activity of EGFR Antibodies. Mol Cancer Ther.11:1467-1476 (2012).
Covell DG, Barbet J, Holton OD, Black CD, Parker RJ, Weinstein JN. Pharmacokinetics of monoclonal immunoglobulin G1, F(ab')2, and Fab' in mice. Cancer Res. 46:3969-78 (1986).
Harris, A. L., "Von Hippel-Lindau Syndrome: Target for Anti-Vascular Endothelial Growth Factor (VEGF) Receptor Therapy," The Oncologist 5(suppl.) 1:32-36 (2000).
Ferrara N, Hillan KJ, Novotny W. Bevacizumab (Avastin), a humanized anti-VEGF monoclonal antibody for cancer therapy. BBRC 333:328-335 (2005).
Al-Rubeai, Mohamed; "Ranibizumab Therapy for Neovascular Age-Related Macular Degeneration," Retinal Physician 1:16-22 (2004).
Huston, J. S., Levinson, D., Mudgett-Hunter, M., Tai, M., Novotny, J., Margolies, M. N., Ridge, R. J., Bruccoleri, R. E., Haber, E., Crea, R., and Oppermann, H. Protein engineering of antibody binding site: Recovery of specific activity in an anti-digoxin single-chain Fv analogue produced in Escherichia coli. Proc. Natl. Acad. Sci. U.S.A. 85:5879-5883 (1988).
Houck KA, Ferrara N, Winer J, Cachianes G, Li B, Leung DW. The vascular endothelial growth factor family: identification of a fourth molecular species and characterization of alternative splicing of RNA. Mol Endocrinol. 5:1806-1814 (1991).
Jain RK. Physiological barriers to delivery of monoclonal antibodies and other macromolecules in tumors. Cancer Res. 50(3 Suppl):814s-819s (1990).
Jin Kim K, Li B, Winer J, Armanini M, Gillett N, Phillips HS, Ferrara N. Inhibition of vascular endothelial growth factor-induced angiogenesis suppresses tumour growth in vivo. Nature 362, 841-844 (1993).
Köhler G, Milstein C. Continuous cultures of fused cells secreting antibody of predefined specificity. Nature. 256:495-497 (1975).
Koch-Nolte, F., et al., "Single Domain Antibodies from Llama Effectively and Specifically Block T Cell Ecto-ADP-Ribosyltransferase ART2.2 In Vivo," FASEB J. 21:3490-3498 (2007).

* cited by examiner

ANTI-HUMAN VEGF ANTIBODIES WITH UNUSUALLY STRONG BINDING AFFINITY TO HUMAN VEGF-A AND CROSS REACTIVITY TO HUMAN VEGF-B

BACKGROUND OF THE INVENTION

1. Field of the Invention

This invention relates generally to anti-human VEGF antibodies with unusually high binding affinity for human VEGF-A and which also cross react with human VEGF-B and particularly to chimeric and humanized versions these antibodies.

2. Description of Related Art

Angiogenesis is a physiological process that involves the growth of new blood vessels from pre-existing ones. This process is vital for growth and development as well as for wound healing. However, it is also fundamental for malignant tumor development and for other non-tumor associated pathologies such as proliferative retinopathies, rheumatoid arthritis and psoriasis (Folkman J. 1971; Praidou A et al. 2010; Canavese M et al. 2010). Vascular endothelial growth factor (VEGF) is a protein secreted by stromal and tumor cells and in a minor proportion by a variety of other cells that plays a key role in stimulation of Angiogenesis (Ferrara N et al. 2004). Over-expression of VEGF can contribute to angiogenesis related diseases. For example, solid cancers cannot grow beyond a limited size without an adequate blood supply and cancers that express VEGF are more capable of growing and metastasizing (Ferrara N. 2005). Taking into account these considerations, anti-angiogenic therapies were developed using anti-VEGF monoclonal antibodies such as Bevacizumab (AVASTIN™) for cancer treatment (Ferrara N et al. 2005) and Ranibizumab (LUCENTIS™) for retinopathy (Ciulla T A et al. 2009). Therapies based in the use of Bevacizumab and Ranibizumab have been extensively studied and applied during the last few years (Van Meter M E et al. 2010; Ciulla T A et al. 2009). Bevacizumab was approved by the U.S. Food and Drug Administration (FDA) for metastatic renal carcinoma, glioblastoma, metastatic colon cancer and non-small cell lung cancer in combination with standard chemotherapy and for use in metastatic breast cancer. However, in the US, a FDA panel of experts has now said they do not see enough of a benefit from AVASTIN™ in advanced breast cancer to justify its serious risks. Several clinical trials are also currently in progress in non-metastatic breast cancer, renal cell carcinoma, glioblastoma multiforme, ovarian cancer, castrate-resistant prostate cancer, non-metastatic unresectable liver cancer and metastatic or unresectable locally advanced pancreatic cancer. Bevacizumab is also used without FDA approval, but on the basis of clinical studies, for treatment of macular degeneration, an eye disease also characterized by proliferation of blood vessels in the retina. Ranibizumab is a Fab antibody fragment derived from the same murine antibody as Bevacizumab and has been approved by the FDA to treat the wet age-related macular degeneration.

In spite of the benefits resulting of the clinical use of the currently approved anti-VEGF-A antibodies, numerous problems remain to be solved regarding to therapeutic effects, side effects, resistance to treatment and cost of treatments. Therefore, development of new more effective anti-human VEGF antibodies is necessary. We have now developed new anti-human VEGF antibodies witch surprisingly have unusually high binding affinity for the human VEGF-A target and cross-reactivity with human VEGF-B. Even thought VEGF-B is strongly related to VEGF-A according to its amino acid sequence, rather than an angiogenic function has a potent survival/antiapoptotic effect required for blood vessel survival (Li X et al. 2009). Therefore, VEGF-B is very important to maintain integrity of the blood vessels which support tumor growth and interference in its action should contribute to a more complete anti-tumor therapy.

SUMMARY OF THE INVENTION

This application describes anti-human VEGF antibodies with unusually strong binding affinity for human VEGF-A and cross reactivity with human VEGF-B, which are stronger inhibitors of the VEGF induced proliferation of endothelial cells in culture as compared with anti-human VEGF antibodies in the art.

The murine anti-human VEGF antibodies disclosed herein binds human VEGF-A with a $K_D$ value of no more than $5 \times 10^{-12}$ M and one humanized version of anti-human VEGF disclose herein binds human VEGF-A with a $K_D$ value of no more than $1.0 \times 10^{-10}$ M. Furthermore, the mouse anti-human VEGF antibodies disclosed herein have an $IC_{50}$ value of about 11 ng/ml for inhibiting VEGF-A induced proliferation of HUVEC endothelial cells in vitro and its humanized version have an $IC_{50}$ value of about 19 ng/ml for inhibiting VEGF-A induced proliferation of HUVEC endothelial cells in vitro. The anti-human VEGF antibodies of the present invention bind to three regions of human VEGF-A$_{165}$ (SEQ ID NO:1) encompassing amino acids residues 16 to 25, 45 to 54 and 79 to 92 of the human VEGF-A$_{165}$ (SEQ ID NO:1). All of these regions are involved in the interaction between VEGF-A and its receptor (VEGFR). In particular amino-acids 16 to 25 of the VEGF-A$_{165}$ are involved in an important contact region (Shalini L et al. 2010). Regarding to this, it has been pointed out that monoclonal antibodies against this region may be very difficult to obtain by the traditional method used to obtain monoclonal antibodies against human VEGF (Jin Kim K et al. 1993) because of the high homology between human and mouse VEGF in the segment comprising amino-acids 16 to 25 (Fuh G et al. 2006). However, a modification in the scheme of immunization disclosed in this invention surprisingly resulted in the obtainment of monoclonal antibodies against this region using the classical method (Kohler et al. 1975). These monoclonal antibodies have unusual high affinity to the VEGF-A molecule and also present cross reactivity with human VEGF-B (SEQ ID NO: 2).

Within the scope of this invention is the use of the humanized version of the antibodies here disclosed for treating VEGF-related angiogenic diseases, including cancer, age-related macular degeneration, rheumatoid arthritis and diabetic retinopathy, by administering to a subject in need of the treatment a therapeutically effective amount of the antibody.

DETAILED DESCRIPTION OF THE INVENTION

Figure 1:
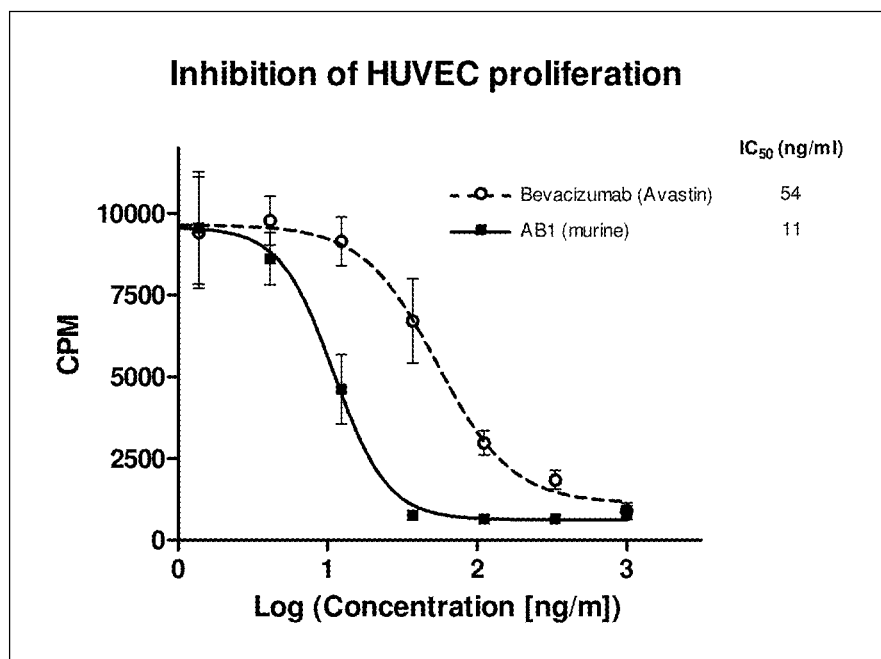
FIG. 1 depicts inhibition of VEGF-induced mitogenesis of a culture of HUVEC cells by the mouse mMcA-AB1-anti-VEGF-A monoclonal antibody of this invention and inhibition of VEGF-induced mitogenesis of a culture of HUVEC cells by the anti-VEGF monoclonal antibody Bevacizumab (AVASTIN™). Experimental procedures were as described in EXAMPLE 5. Each point corresponds to the average and standard deviation of 6 repetitions. $IC_{50}$ values were calculated with the GraphPad Prism 5 program.

The following description of the invention merely intends illustrate several embodiments of the invention. However, by not means these discussed embodiments limit the scope of the invention since many changes and modifications will be apparent to one skilled in the art without departing from the scope of the invention.

ABBREVIATIONS

The following abbreviations are used throughout the present invention: VEGF=vascular endothelial growth factor; VEGF-A=vascular endothelial growth factor variant A; VEGF-B=vascular endothelial growth factor variant B; VEGFR=vascular endothelial growth factor receptor; HUVEC=Human Umbilical Vein Endothelial Cells; KD=dissociation constant of a particular antibody-antigen interaction; BSA=Bovine serum albumin.

DEFINITIONS

The term "human VEGF" as used herein refers to the 165-amino acid vascular cell growth factor (VEGF-$A_{165}$) (SEQ ID NO:1), and described related vascular endothelial growth factors (Leung D W et al 1989, Houck, K A et al 1991) and allelic and processed forms of those growth factors as described (Ferrara N. 1999).

The term "human VEGF-B" as used herein refers to the 186-amino acid vascular cells growth factor variant (VEGF-$B_{186}$) (SEQ ID NO:2) which has a critical role in blood vessel survival during pathological conditions (Zhang F et al. 2009).

The term "antibody" as used herein includes any of the following molecular species: monoclonal antibody, polyclonal antibody, multispecific antibody, or bispecific antibody. A normal antibody comprises two heavy chains and two light chains. Each heavy chain consist of a variable region and a constant region. Each heavy chain has two regions, the constant region and the variable region. Each light chain has also a constant region and a variable region. The variable regions of the light and heavy chains are responsible for antigen binding. The variable region in both chains generally contains three variable loops named complementary determining regions ($CDR_S$). The three $CDR_S$ are inserted between flanking segments named framework region ($FR_S$). The $FR_S$ is significantly more conserved than $CDR_S$.

Antibodies are grouped into different isotypes based on the structure of their heavy chain. There are five major isotypes of antibodies named IgA, IgD, IgE, IgG, and IgM.

The term "antigen-binding fragment" as used herein refers to an antibody fragment the binds to a given antigen but do not comprise a complete antibody. Some, but not all, well known in the art examples of antigen-binding fragments are: Fab, $F(ab')_2$, Fv, and scFv. In certain embodiments, an antigen-binding fragment may comprise one or more CDRs from a specific antibody combined with FRs of one or more human antibodies.

"Fab" refers to an antibody fragment that binds to antigens and it is composed of one constant and one variable domain of each of the heavy and the light chain. In an experimental setting, Fab fragments can be generated by digestion of an antibody with the enzyme papain.

"$F(ab')_2$" refers to an antibody fragment that can be obtained by digestion of an antibody with the enzyme pepsin that cleaves below the hinge antibody region.

"Fv" refers to the smallest fragment of an antibody to bear the complete antigen binding site and that consist of the variable region of the light chain bound to the variable region of the heavy chain of the same antibody.

"scFv" refers to an engineering molecule consisting of two Fv fragments connected by a peptide linker (Huston, J. S. et al. 1988).

The term "epitope" as used herein refers to a special region of an antigen were an antibody binds.

The term "Cancer" as used herein refers to a medical condition involving uncontrollably cell division that results in formation of malignant tumors and metastasis.

The term "angiogenesis" as used herein refers to a physiological process involving the growth of new blood vessels from pre-existing vessels.

The phrase "disease associated with excessive angiogenesis" as used herein refers to a medical condition caused by an abnormal increase in angiogenesis.

Therapeutic Monoclonal Antibodies with High Affinity for its Target Antigen

Monoclonal antibodies affinity for its target antigen is a critical factor to be taken into account for therapeutic performance (Harms B D et al 2012; Lippow M S et al 2007; Zhou Y, et al 2012). Antibodies of higher affinity may be able to be used at lower doses to achieve the desired clinical effects. Lower dosing may allow for more convenient routes of administration and decreased injection volumes, which would translate into lower cost of goods.

Antibodies reported to be of high affinity are generally in the nanomolar range (Griffiths A D, et al 1994; de Haard H J, et al 1999) and occasionally in the sub-nanomolar range (Vaughan T J et al 1996). In particular, the KD of the well known anti-VEGF therapeutic monoclonal antibody AVASTIN™ (bevacisumab) is in the nanomolar range (Presta, L. G., et al 1997).

There are few reports describing monoclonal antibodies with a $K_D$ in the picomolar range and all of them were obtained using non-conventional techniques (Yang W et al 1995; Rathanaswami P et al 2005; Zhao Q et al 2011; Pichinuk E et al 2012).

The present invention provides anti-VEGF monoclonal antibodies which bind human VEGF-$A_{165}$ (SEQ ID NO: 1) with a $K_D$ value of about 5.0 pM in its mouse version, and a $K_D$ of about 100 pM in one humanized version.

Both, the mouse anti-VEGF monoclonal antibody and the humanized version of this invention also have cross-reactivity with human VEGF-B (SEQ ID NO: 2).

The murine version of the monoclonal antibodies of this invention neutralizes VEGF-A in the HUVEC proliferation assay with an IC50 of about 11 ng/ml (five times lower than the IC50 of bevacizumab in the same assay), and the humanized version of the antibodies of this invention in a concentration of about 19 ng/ml (three times lower that the IC50 of bevacizumab in the same assay).

Both, the mouse anti-VEGF monoclonal antibody and the humanized version of this invention have been characterized as possessing superior anti-tumor activity in vivo than Bevacizumab. This is not at all an obvious result since numerous factors determine the anti-tumor activity in vivo (Rudnick S I et al 2009; Beckman R A et al 2007; Covell D G et al 1986; Thurber G M et al 2007; Jain R K et al 1990; Liang W et al 2006). Therefore, the discovery of an antibody with very high affinity and simultaneously very high biological activity in vivo such as the one disclosed herein is highly unpredictable.

Disclosed herein are the parental mice antibody named mMcA-AB1-anti-VEGF-A (mouse monoclonal antibody A-AB1-anti-VEGF-A), the cell line (hybridoma) that produces it named mMcA-AB1-anti-VEGF-A clone, a humanized version of mMcA-AB1-anti-VEGF-A named hMcA-AB1-VEGF-A (humanized monoclonal antibody A-AB1-anti-VEGF-A) and an engineered mini-version of mMcA-AB1-anti-VEGF-A. As discussed below, the parental antibody mMcA-AB1-anti-VEGF-A was obtained using in general the Kohler's method (Kohler G et al 1975) but employing an unusual immunization scheme as described in EXAMPLE 1. In order to select cell clones producing anti-human VEGF-A antibodies of high biological efficiency, the HUVEC proliferation assay was used (for technical description of this assay see EXAMPLE 5). The cell clone (hybridoma) producing the most active antibody was the above mention mMcA-AB1-anti-VEGF-A clone. To our surprise, the monoclonal antibody produced by this cell clone has a very unusual high affinity ($K_D$ in the pM range) for the human VEGF-$A_{165}$ (SEQ ID NO: 1) angiogenic factor as measured using the biacore T100 sensor (for technical description of this assay see EXAMPLE 2). Amino acid sequences of the heavy and light variable chains of mMcA-AB1-anti-VEGF-A are:

Variable Heavy Chain:

```
                                         (SEQ ID NO: 3)
QVKLLESGPELKKPGETVKISCKASGYTFTNFGMNWVKQAPGKG

LKWMGWINTNTGEPTYVDDFKGRFAFSLETSASSAYLQISNLNN

EDTATYFCARYYGSTSVWYFDVWGAGTTVTVSS
```

Variable Light Chain:

```
                                         (SEQ ID NO: 4)
ELVMTQTPSSLSASLGDRVTITCRASQDIFNYLNWYQQKPDGPIK

LLIYYSSRLHSGVPSRFSGSGSGTDYSLTISNLDREDIATYFCQQG

FTLPWTFGGGTKLEIKR
```

CDR Regions are Underlined
(For Technical Description of Sequencing See Example 6)

Epitope analysis indicated that mMcA-AB1-anti-VEGF-A bind the following three segments of the VEGF-$A_{165}$ (SEQ ID NO: 1) amino acid sequence:

1: HHEVVKFMDVYQRSYCH (aa 11 to 27 of VEGF-$A_{165}$) (SEQ ID NO: 13)

2: YIFKPSCVPLMR (aa 44 to 56 of VEGF-$A_{165}$) (SEQ ID NO: 14)

3: QIMRIKPHQGQHIG (aa 79 to 92 of VEGF-$A_{165}$) (SEQ ID NO: 15)

(For Technical Description of Epitope Mapping See Example 3)

Underlined are amino acids described as critical for binding of VEGF-A to its receptor VEGFR-2 (Kiba A et al, 2003). According to this, mMcA-AB1-anti-VEGF-A is the only described monoclonal antibody able to block all the three points of close interaction between VEGF-A and its receptor VEGFR-2. This may explain at least partially the high efficiency of mMcA-AB1-anti-VEGF-A to inhibit VEGF-A activity in biological assays as compared with anti-VEGF antibodies known in the art. For example, mMcA-AB1-anti-VEGF-A exhibited the ability to inhibit HUVEC proliferation to a greater extent than Bevacizumab (see EXAMPLE 5). Also, in inhibition of tumor growth the antibodies of this invention demonstrated to be more effective at the assayed doses than Bevacizumab (see EXAMPLE 10). It is worth mention that all the assayed antibodies lack significant neutralizing activity to mouse VEGF (see EXAMPLE 1) a fact that renders comparison between its anti-tumor activities meaningful. Other anti-VEGF antibodies having neutralizing activity against mouse-VEGF have been compared, regarding to its efficiency to inhibit human tumor growth in nude mice, with Bevacizumab which do not cross-react with mouse-VEGF-A (see U.S. Pat. No. 8,101,177 and U.S. Pat. No. 8,034,905). Therefore, these studies are not adequate to predict the relative efficiency of these antibodies as compared with Bevacizumab in humans. Regarding to this, an illustrative discussion about the contribution of the stromal mouse VEGF to growth of human tumor xenografts can be found in Liang et al (Liang, W. C., et al., "Cross-Species Vascular Endothelial Growth Factor (VEGF)-Blocking Antibodies Completely Inhibit the Growth of Human Tumor Xenografts and Measure the Contribution of Stromal VEGF," J. Biol. Chem. 281(2):951-961 (2006)).

As discussed above, this good performance of mMcA-AB1-anti-VEGF-A in the anti-tumor assay in vivo was not at all obvious because high affinity (or even high inhibition of the activity of VEGF-A in the in vitro UVEC assay) do not necessary correlate with a high increase in the anti-tumor activity in vivo where many other factors may influence activity.

As described below (EXAMPLE 7), a superhumanized version of the parental antibody mMcA-AB1-anti-VEGF-A was obtained. For this, the framework regions between CDRs of mMcA-AB1-anti-VEGF-A were replaced for the most homologous framework regions obtained from IgG genes of human germinal cell lines (Tan P et al. 2002). This methodology introduces minimal mouse amino acid residues in order to avoid immunological reactivity during treatment of humans.

(For Technical Description of the Superhumanization Processes See Example 7).

The sequences of the Variable Heavy and Variable Light chains of the superhumanized version of mMcA-AB1-anti-VEGF-A, named hMcA-AB1-anti-VEGF-A are:

Variable Heavy:

(SEQ ID NO: 5)
QVQLVQSGSELKKPGASVKVSCKAS<u>GYTFTNFGMN</u>WVRQAPGQGLE

WMG<u>WINTNTGEPTYVDDFKG</u>RFVFSLDTSVSTAYLQISSLKAEDTA

VYYCAR<u>YYGSTSVWYFD</u>VWGRGTLVTVSS

Variable Light:

(SEQ ID NO: 6)
DIQMTQSPSSLSASVGDRVTITC<u>RASQDIFNYLN</u>WYQQKPGKAPKL

LIY<u>YSSRLH</u>SGVPSRFSGSGSGTDFTFTISSLQPEDIATYYC<u>QQGF</u>

<u>TLPWT</u>FGQGTKVEIKR

CDR Regions are Underlined

As its parent antibody, hMcA-AB1-anti-VEGF-A exhibited the ability to inhibit HUVEC proliferation to a greater extent than Bevacizumab (see EXAMPLE 9). Also, as its parent antibody, hMcA-AB1-anti-VEGF-A exhibited the ability to inhibit tumor-growth in vivo to a greater extent than Bevacizumab (see EXAMPLE 10). Provided herein in certain embodiments are antibodies and antigen binding fragments that comprise the CDR sequences (SEQ ID NO: 7-12) of mMcA-AB1-anti-VEGF-A as set forth in SEQ ID NO: 5-6.

In certain embodiments, the antibodies provided herein bind VEGF-$A_{165}$ (SEQ ID NO:1) with greater affinity than that of Bevacizumab for VEGF-$A_{165}$. For example, in certain embodiments, the antibodies provided herein bind VEGF-$A_{165}$ with a $K_D$ of about 100 pM and in other embodiments with a $K_D$ of about 5 pM.

The antibodies provided herein have been found to inhibit HUVEC proliferation with greater efficiency than Bevacizumab. For example in certain embodiments, the antibodies herein provided inhibit HUVEC proliferation with an $ID_{50}$ of about 19 ng/ml and in another embodiments with an $ID_{50}$ of about 11 ng/ml. Therefore, the antibodies provided herein may be used to treat various medical conditions associated with increased angiogenesis. For example, the antibodies may be used to treat cancer by inhibiting the proliferation of blood vessels that irrigate a tumor and therefore inhibiting the tumor growth. The anti-tumor efficiency of the antibodies herein provided has been confirmed in vivo (Example 10).

In certain embodiments, the antibodies provided herein inhibit tumor growth at a greater level than Bevacizumab. In in vivo experiments using a xenotransplanted murine tumor model, mMcA-AB1-anti-VEGF-A and hMcA-AB1-anti-VEGF-A inhibited tumor growth with more efficiency than Bevacizumab. Therefore, in certain embodiments, the antibodies provided herein may be used at similar dosage that Bevacizumab to achieve a better antitumor effect or at lesser dosage to avoid secondary undesirable side effects with similar effectivity.

The antibodies disclosed herein may be used in the treatment of medical conditions caused by excessive angiogenesis caused by excessive expression of VEGF. Examples of these conditions include wet AMD and diabetic retinopathy as ocular diseases and several tumoral diseases (Crawford T N et al, 2009; Albini A et al, 2012). Cancer conditions that may be treated with the antibodies disclosed herein include but are not limited to carcinoma, blastoma, sarcoma, germ cell tumor, or hematological or lymphoid malignancy such as leukemia, lymphoma, or multiple myeloma. More specifically, cancerous conditions and tumor types that may be treated using the antibodies disclosed herein include but are not limited to squamous cell cancer, lung cancer (e.g., small cell lung cancer, non-small cell lung cancer (NSCLC), adenocarcinoma of the lung, or squamous cell carcinoma of the lung), cancer of the peritoneum, liver cancer (e.g., hepatocellular carcinoma/hepatoma), gastric or stomach cancer (e.g., gastrointestinal cancer), pancreatic cancer, brain tumor (e.g., glioblastoma/glioblastoma multiforme (GBM), non-glioblastoma brain tumor, or meningioma), glioma (e.g., ependymoma, astrocytoma, anaplastic astrocytoma, oligodendroglioma, or mixed glioma such as oligoastrocytoma), cervical cancer, ovarian cancer, liver cancer (e.g., hepatoblastoma, hepatocellular carcinoma/hepatoma, or hepatic carcinoma), bladder cancer (e.g., urothelial cancer), breast cancer, colon cancer, colorectal cancer, rectal cancer, endometrial or uterine carcinoma, salivary gland carcinoma, kidney or renal cancer (e.g., rhabdoid tumor of the kidney), prostate cancer, vulval cancer, penile cancer, anal cancer (e.g., anal squamous cell carcinoma), thyroid cancer, head and neck cancer (e.g., nasopharyngeal cancer), skin cancer (e.g., melanoma or squamous cell carcinoma), osteosarcoma, Ewing's sarcoma, chondrosarcoma, soft tissue sarcoma (e.g., rhabdomyosarcoma, fibrosarcoma, Kaposi's sarcoma), carcinoid cancer, eye cancer (e.g., retinoblastoma), mesothelioma, lymphocytic/lymphoblastic leukemia (e.g., acute lymphocytic/lymphoblastic leukemia (ALL) of both T-cell lineage and B-cell precursor lineage, chronic lymphoblastic/lymphocytic leukemia (CLL), acute myelogenous/myeloblastic leukemia (AML), including mast cell leukemia, chronic myelogenous/myelocytic/myeloblastic leukemia (CML), hairy cell leukemia (HCL), Hodgkin's disease, non-Hodgkin's lymphoma, chronic myelomonocytic leukemia (CMML), follicular lymphoma (FL), diffuse large B cell lymphoma (DLBCL), mantle cell lymphoma (MCL), Burkitt's lymphoma (BL), mycosis fungoides, Sezary syndrome, cutaneous T-cell lymphoma, mast cell neoplasm, medulloblastoma, nephroblastoma, solitary plasmacytoma, myelodysplastic syndrome, chronic and non-chronic myeloproliferative disorder, central nervous system tumor, pituitary adenoma, vestibular schwannoma, primitive neuroectodermal tumor, ependymoma, choroid plexus papilloma, polycythemia vera, thrombocythemia, idiopathic myelofibrosis, and pediatric cancers such as pediatric sarcomas (e.g., neuroblastoma, rhabdomyosarcoma, and osteosarcoma). In addition, tumors can be malignant (e.g., cancers) or benign (e.g., hyperplasia, cyst, pseudocyst, hamartoma, and benign neoplasm).

Other conditions that may be treated by the antibodies and antigen-binding fragments described herein include inflammatory conditions such as rheumatoid arthritis, psoriasis, scleroderma, chronic obstructive pulmonary disease, and asthma. In other non-therapeutic embodiments, the antibodies or antigen-binding fragments may be used in various in vitro or in vivo diagnostic or detection applications.

The antibodies disclosed herein may be administered alone or in combination with one or more additional therapeutic agents. For example, the antibodies or antigen-binding fragments disclosed herein may be administered in combination with chemotherapy, radiation therapy and cancer surgery. Furthermore, the antibodies or antigen-binding fragments disclosed herein may be administered in combination with treatments for complications arising from chemotherapy or other therapeutic agents. In certain embodiments, the antibodies or antigen-binding fragments disclosed herein may be administered as part of the same pharmaceutical composition.

In certain embodiments, conjugates linked to the antibodies or antigen-binding fragments disclosed herein may comprise one or more agents meant to alter one or more pharmacokinetic (PK) properties of the antibody or antigen-binding fragment, such as for example polyethylene glycol (PEG) to increase the half-life.

In certain embodiments, compositions are provided comprising antibodies disclosed herein in combination with one or more cytokines. Example of cytokines include but are not limited to lymphokines, monokines, human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, fibroblast growth factor, prolactin, placental lactogen, tumor necrosis factor .alpha. and .beta., mullerian-inhibiting substance, mouse gonadotropin-associated peptide, inhibin, activin, integrin, thrombopoietin (TPO), nerve growth factors such as NGF-.beta., platelet growth factor, transforming growth factors such as TGF-.alpha. and TGF-.beta., insulin-like growth factor I and II, erythropoietin (EPO), osteoinductive factors, interferons such as interferon-.alpha., -.beta., and -.gamma., colony stimulating factors such as macrophage-CSF, granulocyte macrophage CSF, and granulocyte-CSF, interleukins such IL-1, IL-1.alpha., IL-2, IL-3, IL-4, IL-5, IL-6, IL-7, IL-8, IL-9, IL-10, IL-11, and IL-12, tumor necrosis factors such as TNF-.alpha. and TNF-.beta., and other polypeptide factors. The antibodies or antigen-binding fragments disclosed herein may be provided and/or administered in combination with any cytokine, including any of those listed above.

In certain embodiments, compositions are provided comprising antibodies or antigen-binding fragments disclosed herein linked to or in combination with one or more chemotherapeutic agents. Examples of chemotherapeutic agents include, but are not limited to, ALT-110, AMN-107 (Nilotinib), amrubicin, ARQ-197, atrasentan (Xinlay®), AV-299, AZD 1152, AZD 2171, batabulin, BIO-111, BIO-140, calcitriol, CC 8490, cilengitide, dasatinib, decatanib, DN-101, edotecarin, enzastaurin, erlotinib, everolimus, gimatecan, gossypol (e.g., gossypol acetate), GSK461364, GSK690693, IL13-PE38QQR, INO 1001, IPdR, ipilimumab, KRX-0402, Lep-etu, lonafarnib, lucanthone, LY 317615, MK-0457, MLN8054, neuradiab, nolatrexed, oblimersen, ofatumumab, ON 0910.Na, oregovomab, panitumumab, pazopanib, PHA-739358, R-763, RTA 744, rubitecan, Sdx 102, talampanel, temsirolimus, tesmilifene, tetrandrine, ticilimumab, TKI-258, TLK 286, trabectedin, vandetanib, vitespan, Xr 311, zanolimumab, 131-I-TM-601, and zolendronate, histrelin, azacitidine, dexrazoxane, alemtuzumab, lenalidomide, gemtuzumab, ketoconazole, nitrogen mustard, ibritumomab tiuxetan, decitabine, hexamethylmelamine, bexarotene, tositumomab, arsenic trioxide, editronate, cyclosporine, Edwina-asparaginase, strontium 89, romidepsin (FK-228), ADS-100380, CG-781, CG-1521, IMT504, IMT506, IMT507, SB-556629, chlamydocin, vorinostat, etoposide, gemcitabine, doxorubicin, 5'-deoxy-5-fluorouridine, vincristine, temozolomide, camptothecin, irinotecan, oxaliplatin, tamoxifen, anastrazole, diethylstilbestrol, Bevacizumab, leuprolide, sunitinib, medroxyprogesterone, raloxifene, bicalutamide, flutamide, amifostine, NVP-LAQ824, suberoyl analide hydroxamic acid, valproic acid, trichostatin A, FK-228, SU11248, BAY43-9006, KRN951, aminoglutethimide, amsacrine, anagrelide, anastrozole, asparaginase, *bacillus* Calmette-Guerin (BCG) vaccine, bleomycin, buserelin, busulfan (1,4-butanediol dimethanesulfonate), satraplatin, carboplatin, carmustine, chlorambucil, cisplatin, cladribine, clodronate, cyclophosphamide, cyproterone, cytarabine, dacarbazine, dactinomycin, daunorubicin, diethylstilbestrol, epirubicin, fludarabine, fludrocortisone, fluoxymesterone, fluta-mide, hydroxyurea, idarubicin, ifosfamide, imatinib, leucovorin, leuprolide, levamisole, lomustine, mechlorethamine, melphalan, mercaptopurine, mesna, methotrexate, mitomycin, mitotane, mitoxantrone, nilutamide, octreotide, edotreotide, oxaliplatin, pamidronate, Pentostatin, plicamycin, porfimer, procarbazine, raltitrexed, rituximab, streptozocin, teniposide, testosterone, thalidomide, thalidomide combined with dexamethasone, thioguanine, thiotepa, tretinoin, vindesine, all trans-retinoic acid, or 13-cis-retinoic acid, phenylalanine mustard, uracil mustard, estramustine, altretamine, floxuridine, 5-deooxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin, diftitox, gefitinib, bortezimib, paclitaxel, docetaxel, epithilone B, BMS-247550, BMS-310705, droloxifene (3-hydroxytamoxifen), 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, LY294002, LY292223, LY292696, LY293684, LY293646, wortmannin, BAY-43-9006, ZM336372, L-779,450, flavopiridol, UCN-01, rapamycin, everolimus.

In certain embodiments, an antibody provided herein is in combination with one or more of pegylated or unpegylated interferon alfa-2a, pegylated or unpegylated interferon alfa-2b, pegylated or unpegylated interferon alfa-2c, pegylated or unpegylated interferon alfa n-1, pegylated or unpegylated interferon alfa n-3, and pegylated, unpegylated consensus interferon or albumin-interferon-alpha.

Compositions comprising an antiemetic are useful for preventing or treating nausea; a common side effect of chemotherapy. Accordingly, in certain embodiments compositions are provided that comprise an antibody provided herein linked to or in combination with one or more anti-cancer agents and one or more antiemetics, including but not limited to casopitant, Netupitant, palonosetron, aprepitant, diphenhydramine, hydroxyzine, metoclopramide, lorazepam, alprazolam, haloperidol, droperidol, dronabinol, dexamethasone, prednisolone, methylprednisolone, prochlorperazine, granisetron, ondansetron, dolasetron and tropisetron.

Other side effects of cancer treatment include red and white blood cell deficiency. Accordingly, compositions are provided that comprise an antibody provided herein linked to or in combination with an agent that treats red and/or white blood cell deficiency such as G-CSF, pegylated G-CSF, GM-CSF, erythropoietin and pegylated erythropoietin.

In certain embodiments, compositions are provided that comprise an antibody provided herein in combination with one or more anti-hypertensive agents such as a diuretic, an adrenergic receptor antagonist, an adrenergic receptor agonist, a calcium channel blockers, an ACE inhibitor, an angiotensin II receptor antagonist, an aldosterone antagonist, a vasodilator, or a centrally acting adrenergic drug.

In certain embodiments, the antibodies disclosed herein may be administered as part of a pharmaceutical composition that comprises one or more physiologically tolerable components. Therefore, in certain embodiments, such compositions and methods of formulating such compositions are provided herein. Compositions comprising one or more antibodies disclosed herein and one or more physiologically tolerable components may be used in the treatment of diseases associated with increased angiogenesis.

Examples of physiologically tolerable components for use in the pharmaceutical compositions disclosed herein are: pharmaceutically acceptable liquid, gel, or solid carriers, diluents, adjuvants, excipients, auxiliary substances and other components known in the art, or combinations thereof. Examples of suitable components are: antioxidants, fillers, binders, disintegrants, buffers, preservatives, lubricants, flavorings, thickeners, coloring agents, or emulsifiers. Examples of suitable antioxidants are: methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and propyl gallate. Examples of suitable carriers are: aqueous vehicles such as physiological sodium chloride, Ringer's solution, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcellulose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The term "therapeutically effective amount" or "effective dosage" as used herein refers to the dosage or concentration of a drug effective to treat a disease or condition. For example, with regard to the use of the antibodies disclosed herein to treat cancer, a therapeutically effective amount is the dosage or concentration of the antibody or antigen-binding fragment capable of eradicating all or part of a tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

The effective dosage of an antibody or antigen-binding fragment provided herein may be determined using methods well known in the art. For example, the effective dosage may be established by determining whether a tumor being treated in a subject shrinks, ceases to grow, or grows more slowly following administration at a particular dosage.

In certain embodiments, an antibody as provided herein may be administered at a therapeutically effective dosage of about 0.01 μg/mouse to about 100 μg/mouse. A given dosage may be administered at various intervals, such as for example once a day, two or more times per day, two or more times per week, once per week, once every two weeks, once every three weeks, once a month, or once every two or more months. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

Pharmaceutical compositions comprising the antibodies disclosed herein, and in certain embodiments in combination with chemotherapeutic agents, may be prepared by methods well known in the art.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes. In embodiments wherein the antibodies are administered via injection, injectable pharmaceutical compositions may be prepared in any conventional form, such as for example liquid solution, suspension, emulsion, or solid forms suitable for generating liquid solution, suspension, or emulsion. Preparations for injection may include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-VEGF antibody or composition thereof.

Reconstitution of a lyophilized powder with water for injection provides a formulation for use in parenteral administration. In one embodiment, for reconstitution the lyophilized powder is added to sterile water or other liquid suitable carrier. The precise amount depends upon the selected therapy being given, and can be empirically determined.

In certain embodiments, systems and methods are provided for production of the antibodies disclosed herein. The mouse antibody mMcA-AB1-anti-VEGF-A of this invention can be produced by culturing the cell clone (hybridoma) producing mMcA-AB1-anti-VEGF-A, in vitro or in vivo, using standard techniques well known in the art (See for example Birch J R et al 1985). Alternatively, an expression system can be used. DNA encoding the parental mouse monoclonal antibody of this invention, can be isolated from the producer cells or synthesized in vitro, inserted in a cloning vector and introduced into a suitable host cell or bacteria using standard procedures (Davies S L. 2009, Volume 6, 153-173).

Non-natural versions of the mouse parental antibody disclosed herein (e.g. chimeric antibodies, humanized antibodies, or single chain antibodies) can be prepared using methods well known in the art (Morrison S L et al 1984; Neuberger M S et al 1984; Takeda S et al 1985). Expression systems can be also used to produce the different antibody derivatives of the mouse parental monoclonal antibody disclosed herein. These expression systems include polynucleotides encoding the antibodies, vectors comprising these polynucleotides, and host cells comprising these vectors. Polynucleotides encoding the antibodies disclosed herein may be isolated or synthesized using methods well known in the art, and inserted into a replicable vector for amplification or cloning.

Polynucleotides encoding variable light ($V_L$) and variable heavy ($V_H$) chains of the antibodies may be expressed from a single vector, or they may be expressed using two separate vectors, followed by in vitro assembly. In certain embodiments, they may be co-expressed from two separate vectors within the same cell and assembled intracellularly. Suitable vectors may contain various configurations of one or more regulatory sequences, such as promoters, enhancers, or transcription initiation sequences, as well as genes encoding markers for phenotypic selection. Vectors having suitable backbones for expression of the antibodies disclosed herein are known in the art (See for example Davies S L et al, 2009). In certain embodiments, the vector may contain a polynucleotide sequence encoding the constant regions of the heavy chain ($C_H$) and light chain ($C_L$) of a human IgG immunoglobulin. Alternatively, the vector may express only the $V_H$ and $V_L$ chains of the antibody, with the expressed polypeptide comprising an Fv fragment rather than a whole antibody. Vectors may be inserted into a suitable host cell for amplification or expression of the polynucleotide sequence. The host cells may be cultured for antibody production in a variety of media known in the art, such as for example Minimal Essential Medium (MEM) (Sigma), RPMI-1640 (Sigma), Dulbecco's Modified Eagle's Medium (DMEM) (Sigma), and Ham's F10 (Sigma). Media may be supplemented with a variety of agents, such as for example hormones, growth factors, salts, buffers, nucleotides, antibiotics, trace elements, glucose, or other energy sources. Culture conditions such as temperature and pH may be adjusted using parameters well known in the art. Following expression, one or more antibodies may be purified using methods well known in the art (See for example Vijayalakshmi M A. 1998).

The antibodies disclosed herein may comprise conjugates for specific delivery to the tumor location.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Generation of Anti-VEGF Monoclonal Antibody

Monoclonal antibodies were generated in general according to Kohler's method (Kohler G et al 1975). However, the immunization scheme was unusual. In brief 4 week-old BALB/c female mice were injected once a month for a period of 10 months with human recombinant $VEGF_{165}$ (SEQ ID NO:1) conjugated with cationized BSA (Imject® BSA and EDC Conjugation Kits, Pierce, France) in aluminum hydroxide solution (Imject® Alu, Pierce). Lymphocytes were harvested and fused with myeloma cells by treatment with polyethylene glycol (PEG 1500, BDH). After this, hybridoma cells were seeded and grown in HAT medium (hypoxanthine aminopterin thymidine, Sigma). The presence of specific antibodies was detected by direct ELISA against VEGF-A without BSA. A limited dilution method was used to select anti-humanVEGF antibody producing clones. Afterward, in order to select cell clones producing anti-humanVEGF-A antibodies of very high affinity, the HUVEC proliferation assay was used.

Using this methodology, several candidate hibridomas were isolated and frozen. One of them, named mMcA-AB1-anti-VEGF-A clone was further studied. Monoclonal antibody produced by this mMcA-AB1-anti-VEGF-A hibridoma was named mMcA-AB1-anti-VEGF-A (in short mouse AB1 antibody). Purification of this antibody was performed by standard techniques (Vijayalakshmi M A. 1998) including affinity chromatography using a protein-G Sepharose column (HiTrap Protein GHP. GE Healthcare). The mouse AB1 antibody of this invention and its derivatives do not cross-react or neutralize mouse VEGF-A as measured by ELISA and Surface Plasmon Resonance.

Example 2

Determination of the Dissociation Rate Constant ($K_D$) of the Complex mMc-AB1-Anti-VEGF-A/VEGF-$A_{165}$ The affinity between the purified mouse monoclonal antibody mMc-AB1-anti-VEGF-A of this invention and VEGF-$A_{165}$ (SEQ ID NO: 1) protein was determined by surface plasmon resonance (SPR). Affinity and Dissociation Constants of the complex mMc-AB1-anti-VEGF-A/VEGF-$A_{165}$, $K_A$ and $K_D$, respectively, were determined by kinetic analysis fitting a 1:1 interaction model using the Biacore T100 evaluation software. Results are shown in Table 1.

TABLE 1

| Kinetic parameters of the interaction mMcA-AB1-anti-VEGF-A/VEGF-$A_{165}$ | | | |
|---|---|---|---|
| $k_a$ (1/Ms) | $k_d$ (1/s) | $K_D$ (1/M) | $K_A$ (M) |
| $1.87 \pm 0.02 \times 10^7$ | $9.9 \pm 0.4 \times 10^{-5}$ | $5.3 \times 10^{-12}$ | $1.9 \times 10^{11}$ |

This result indicates that the mMc-AB1-anti-VEGF-A monoclonal antibody of this invention have an unusually high (in the pM range) affinity for human VEGF-A.

Example 3

Mapping of VEGF-$A_{165}$ Epitopes Recognized by mMc-AB1-Anti-VEGF-A

Mapping of VEGF-$A_{165}$ epitopes recognized by mMc-AB1-anti-VEGF-A was performed by LC Sciences (Huston, Tex.) using its PeptArray™ system. Overlapping peptides were synthesized according to the VEGF$_{165}$ sequence (SEQ ID NO: 1). Conditions were: Binding buffer: 1×PBS, pH 7.0; Washing buffer: 1×PBS with 0.05% Tween-20 and 0.05%

Triton X-100, pH 7.0. Binding condition was: 1 μg/mL mMc-AB1-anti-VEGF-A in binding buffer at 25° C., 1 hour. Detection condition was: 10 ng/mL goat anti-mouse IgG Cy5 conjugate in binding buffer at 25° C., 30 min. Scanning was at PMT 700 in a 635 nm channel. Results of this analysis indicated main contact of mMc-AB1-anti-VEGF-A with three VEGF-$A_{165}$ (SEQ ID NO: 1) domains:

1: HHEVVK_F_MDVYQRSYCH (aa 11 to 27 of VEGF-$A_{165}$) (SEQ ID NO: 13)

2: Y_IF_KPSCVPLMR (aa 44 to 56 of VEGF-$A_{165}$) (SEQ ID NO: 14)

3: QIMR_IK_PHQGQHIG (aa 79 to 92 of VEGF-$A_{165}$) (SEQ ID NO: 15)

Underlined are amino acids described as critical for binding of VEGF-A to its receptor VEGFR-2 (Kiba A et al 2003).

Example 4

Cross-Reactivity of mMcA-AB1-Anti-VEGF-A with Human VEGF-$B_{186}$ (SEQ ID NO: 2)

mMcA-AB1-anti-VEGF-A (6.30-0.18 μM) was injected over immobilized Vascular endothelial growth factor antigen B (VEGF-$B_{186}$) (4000 RU). $K_A$ and $K_D$ respectively, were determined by kinetic analysis fitting a 1:1 interaction model using biacore T100 Evaluation software. Kinetic parameters and constants are shown in Table 2.

TABLE 2

Kinetic parameters of the interaction between mMcA-AB1-anti-VEGF-A and VEGF-$B_{186}$.

| $k_a$ (1/Ms) | $k_d$ (1/s) | $K_D$ (1/M) | $K_A$ (M) |
|---|---|---|---|
| 32.80 ± 0.06 × 10$^4$ | 5.71 ± 0.02 × 10$^{-3}$ | 1.8 × 10$^{-7}$ | 5.6 × 10$^6$ |

This result indicates that mMcA-AB1-anti-VEGF-A is able to cross-react with VEGF-$B_{186}$ albeit with low affinity as compared with its affinity for VEGF-A.

Example 5

Neutralization Activity of mMcA-AB1-Anti-VEGF-A on the VEGF-A Induced Proliferation of HUVEC in Culture HUVEC cells were seeded in 96 well plates at a density of 2500 cells/well containing 50 ul of M199 media supplemented with 10% FCS and 50 ug/ml gentamicin. After 2 h, 100 ul of a solution containing 25 ul of purified mMcA-AB1-anti-VEGF-A in RPMI media and 75 ul of M199 complete media containing VEGF (20 ng/ml) were added to each well. After 24 h incubation 25 ul of M199 complete media containing 2.5 μCi/ml methyl-[$^3$H]-thymidine was added and incubation continued for additional 48 h. After this, 50 ul of 6 M guanidinium chloride was added to stop the reaction. Cellular brakeage was completed with three frozen-thaw cycles, DNA was collected in Whatman-GFC filters and radioactivity measured. FIG. 1 shows a plot comparing the neutralization capacity of the mMcA-AB1-anti-VEGF-A monoclonal antibody of this invention and the neutralization capacity of the anti-VEGF monoclonal antibody Bevacizumab in the art (Zondor S D et al 2004).

Example 6

Variable Heavy and Variable Light Chains Sequences of mMcA-AB1-Anti-VEGF-A

To obtain the sequence of the genes codifying the variable heavy and light chains of mMcA-AB1-anti-VEGF-A, total RNA was extracted from hybridoma cells producing the antibody by the TRIzol (Gibco) method. The cDNA was synthesized using reverse transcriptase (Promega) with random primers (Invitrogen). Amplification of the variable heavy and light chains of the Fab region was carried out as described (Sastry L. 1989).

Primers Used for Amplification of the Variable Heavy Chain (5' End):

```
                                          (SEQ ID NO: 16)
CPV 1.
5'-AGGT(C/G)(C/A)A(G/A)CT(G/T)CTCGAGTC(T/A)GG-3'

(SEQ ID NO: 17)
CPV 2.
5'-AGGTCCAGCTGCTCGAGTCTGG-3'

(SEQ ID NO: 18)
CPV 3.
5'-AGGTCCAGCTGCTCGAGTCAGG-3'

(SEQ ID NO: 19)
CPV 4.
5'-AGGTCCAGCTTCTCGAGTCTGG-3'

(SEQ ID NO: 20)
CPV 5.
5'-AGGTCCAGCTTCTCGAGTCAGG-3'

(SEQ ID NO: 21)
CPV 6.
5'-AGGTCCAACTGCTCGAGTCTGG-3'

(SEQ ID NO: 22)
CPV 7.
5'-AGGTCCAACTGCTCGAGTCAGG-3'

(SEQ ID NO: 23)
CPV 8.
5'-AGGTCCAACTTCTCGAGTCTGG-3'

(SEQ ID NO: 24)
CPV 9.
5'-AGGTCCAACTTCTCGAGTCAGG-3'

(SEQ ID NO: 25)
CPV 10.
5'-AGGTCGAACTTCTCGAGTC(T/A)GG-3'
```

Primer Used for Amplification of the Variable Heavy Chain (3' End):

```
                                          (SEQ ID NO: 26)
:5'-AGGCTTTACTAGTACAATCCCTGGGCACAATT-3'
```

Primers Used for Amplification of the Variable Light Chain (5' End):

```
                                          (SEQ ID NO: 27)
CLV 1.
5'-CCAGTTCCGAGCTCGTGCTCACCCAGTCTCCA-3'

(SEQ ID NO: 28)
CLV 2.
5'-CCAGTTCCGAGCTCCAGATGACCCAGTCTCCA-3'
```

-continued

```
                                               (SEQ ID NO: 29)
CLV 3.
5'-CCAGATGTGAGCTCGTGATGACCCAGACTCCA-3'

(SEQ ID NO: 30)
CLV 4.
5'-CCAGATGTGAGCTCGTCATGACCCAGTCTCCA-3'

(SEQ ID NO: 31)
CLV 5.
5'-CCAGTTCCGAGCTCGTGATGACACAGTCTCCA-3'
```

Primer Used for Amplification of the Variable Heavy Chain (3' End):

```
                                               (SEQ ID NO: 31)
5'-GCGCCGTCTAGAATTAACACTCATTCCTGTTGAA-3'
```

The resulting products were cloned into the pComb 3 vector (Barbas, C. F. 1991) and sequenced. The deduced amino acid sequences of the variable heavy and light chains of the mouse anti-VEGF AB1 monoclonal antibody of the invention results as follows:

Variable Heavy

```
                                                (SEQ ID NO: 3)
QVKLLESGPELKKPGETVKISCKASGYTFTNFGMNWVKQAP

GKGLKWMGWINTNTGEPTYVDDFKGRFAFSLETSASSAYLQ

ISNLNNEDTATYFCARYYGSTSVWYFDVWGAGTTVTVSS
```

Variable Light

```
                                                (SEQ ID NO: 4)
ELVMTQTPSSLSASLGDRVTITCRASQDIFNYLNWYQQKPD

GPIKLLIYYSSRLHSGVPSRFSGSGSGTDYSLTISNLDRED

IATYFCQQGFTLPWTFGGTKLEIKR
```

Note: CDR Regions are Underlined

Example 7

Humanization of mMcA-AB1-Anti-VEGF-A

For mMcA-AB1-anti-VEGF-A humanization, the framework regions between CDRs were replaced for the most homologous framework regions obtained from IgG genes of human germinal cell lines (Tan P et al 2002). This methodology introduces minimal mouse amino acid residues in order to avoid immunological reactivity during treatment of humans. For homology studies the used data base was IMGT. Designed genes containing codifying CDRs of mMcA-AB1-anti-VEGF-A and framework regions of IgG genes of human germinal cell lines as well as a secretion signal were synthesized by a commercial synthesis service (GenScript Corporation). The synthetic gene corresponding to the humanized variable heavy region was inserted into the EcoRI and NheI sites of the pFUSE-CHIg-hG1 vector (InvivoGen) and the synthetic gene corresponding to the humanized variable light region was inserted into the BtsEII and BsiWI sites of the pFUSE2-CLIg-hk vector (InvivoGen). Both vectors provide the human constant regions necessary to complete the heavy (pFUSE-CHIg-hG1) and the light (pFUSE2-CLIg-hk) human IgG chains in order to obtain the humanized antibody. Furthermore, plasmids pFUSE-CHIg-hG1-P and pFUSE2-CLIg-hk-P were cotransfected into NS0 cells using Lipofectamine 2000 (Invitrogen). Cell clones expressing anti-VEGF antibody activity were selected and one of them used for antibody production and purification using methods well known in the art.

The Variable Heavy and Variable Light chains sequences of the humanized version of mMcA-AB1-anti-VEGF-A are as follows:

Variable Heavy:

```
                                                (SEQ ID NO: 5)
QVQLVQSGSELKKPGASVKVSCKASGYTFTNFGMNWVRQAPG

QGLEWMGWINTNTGEPTYVDDFKGRFVFSLDTSVSTAYLQIS

SLKAEDTAVYYCARYYGSTSVWYFDVWGRGTLVTVSS
```

Variable Light:

```
                                                (SEQ ID NO: 6)
DIQMTQSPSSLSASVGDRVTITCRASQDIFNYLNWYQQKPGKA

PKLLIYYSSRLHSGVPSRFSGSGSGTDFTFTISSLQPEDIATY

YCQQGFTLPWTFGQGTKVEIKR
```

Note: CDR Regions are Underlined

Example 8

Determination of the Dissociation Rate Constant ($K_D$) of the Complex Humanized Version of mMc-AB1-Anti-VEGF-A/VEGF-A$_{165}$ The affinity between the humanized version of mMcA-AB1-anti-VEGF-A and VEGF-A$_{165}$ (SEQ ID NO: 1) was determined by surface plasmon resonance (SPR). Affinity and Dissociation Constants, $K_A$ and $K_D$, respectively, were determined by kinetic analysis fitting a 1:1 interaction model using the BIAcore T100 evaluation software. Results are shown in Table 3.

TABLE 3

| Kinetic parameters of the interaction humanized mMc-AB1-anti-VEGF-A/VEGF-A$_{165}$ | | | |
|---|---|---|---|
| $k_a$ (1/Ms) | $k_d$ (1/s) | $K_D$ (1/M) | $K_A$ (M) |
| $3.83 \pm 0.03 \times 10^6$ | $4.21 \pm 0.02 \times 10^{-4}$ | $1.09 \times 10^{-10}$ | $9.24 \times 10^5$ |

Example 9

Figure 2:
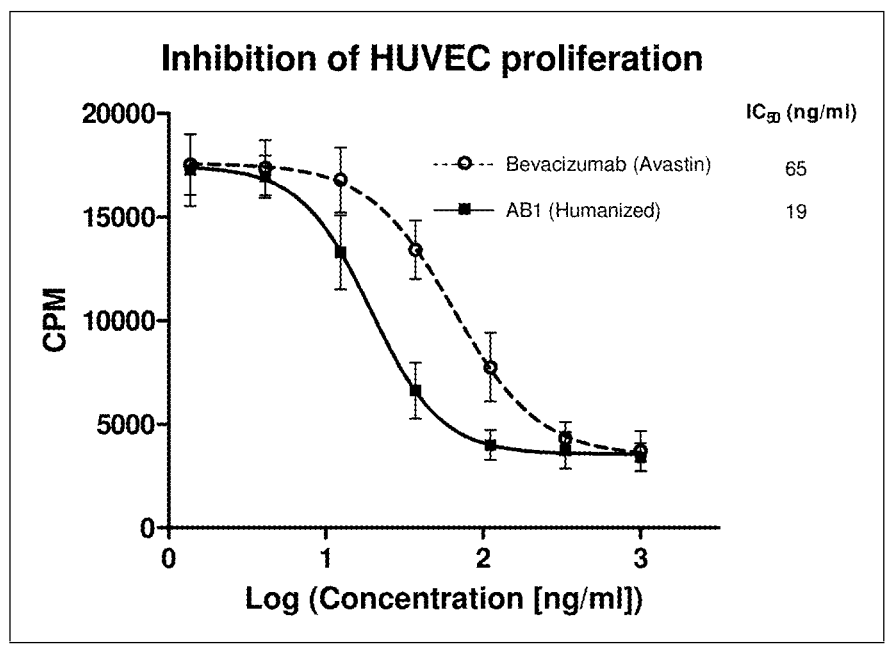
FIG. 2 depicts inhibition of VEGF-induced mitogenesis of a culture of HUVEC cells by the humanized version of the mouse mMcA-AB1-anti-VEGF-A monoclonal antibody of this invention and inhibition of VEGF-induced mitogenesis by the anti-VEGF monoclonal antibody Bevacizumab (AVASTIN™). Experimental procedures are described in EXAMPLE 5. Each point corresponds to the average and standard deviation of 6 repetitions. $IC_{50}$ values were calculated with the GraphPad Prism 5 program.

Neutralization Activity of Humanized mMcA-AB1-Anti-VEGF-A on the VEGF-A Induced Proliferation of HUVEC in Culture HUVEC cells were seeded in 96 well plates at a density of 2500 cells/well containing 50 ul of M199 media with addition of 10% FCS and 50 ug/ml gentamicin. After 2 h, 100 ul of a solution containing 25 ul of purified antibody in RPMI media and 75 ul of M199 complete media containing VEGF (20 ng/ml) were added to each well. After 24 h incubation 25 ul of M199 complete media containing 2.5 µCi/ml methyl-[$^3$H]-thymidine was added and incubation continued for additional 48 h. After this, 50 ul of 6 M guanidinium chloride were added to stop the reaction. Cellular brakeage was completed with three cycles of frozen-thaw DNA was collected in Whatman GFC filters and radioactivity measured. FIG. 2 shows a plot comparing the neutralization capacity of the humanized mMcA-AB1-anti-VEGF-A on the VEGF-A induced proliferation of HUVEC in culture. and the neutralization capacity of the anti-VEGF monoclonal antibody Bevacizumab in the art.

Example 10

In Vivo Activity of the Anti-VEGF Antibodies

IIB-Mel-J cells (Guerra, L., et al., Characterization of IIB-MEL-J: a new and highly heterogeneous human melanoma cell line. Pigment Cell Res, 1989. 2(6): p. 504-9) were used to study the tumor growth inhibition in nude mice. IIB-Mel-J cells were maintained in culture with DMEM medium, supplemented with 10% FBS and 5 µg/ml insulin and 50 µg/ml gentamycin. Cells were grown at 37° C., in 5% CO2 until confluence, harvested, counted, washed and resuspended in sterile Matrigel at a concentration of 50×106 cell/ml. Xenografts were established in 4-6 week-old Nude Swiss mice by injecting 5×106 IIB-Mel-J cells into the dorsal flank of the mice. After 6 days were tumors were palpable, mice were randomly distributed into 10 groups (n=10) and intraperitoneally injected twice weekly with either PBS (control group) or different antibodies in PBS in three different concentrations each as follows: group A, mice injected with 0.1 ml of PBS; group B, mice injected with 0.1 ml of the AB1 antibody at a dose of 1 µg/mouse; group C, mice injected with 0.1 ml of the AB1 antibody at a dose of 25 µg/mouse; group D, mice injected with 0.1 ml of the humanized version of AB1 antibody at a dose of 1 µg/mouse; group E, mice injected with 0.1 ml of the humanized version of AB1 antibody at a dose of 25 µg/mouse; group F, mice injected with 0.1 ml of the humanized version of Bevacizumab (AVASTIN™) at a dose of 1 µg/mouse and group G, mice injected with 0.1 ml of the AVASTIN™ antibody at a dose of 25 µg/mouse. Tumor growth was followed measuring length and width with a caliber instrument and the volume estimated with the following formula: ½ length×width².

Figure 3:
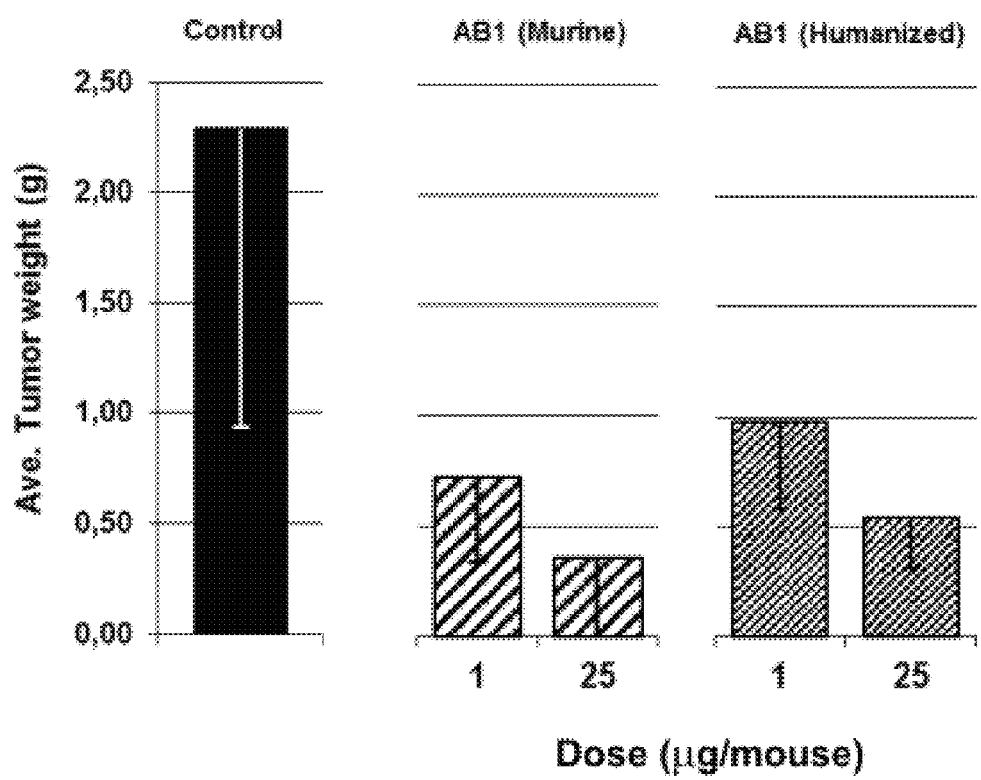
FIG. 3 depicts inhibition of IIB-Mel-J tumor growth in nude mice after treatment with the mouse mMcA-AB1-anti-VEGF-A monoclonal antibody of this invention and with the humanized version of the mouse mMcA-AB1-anti-VEGF-A monoclonal antibody of this invention at the following doses: 1 μg/mouse or 25 μg/mouse, twice a week for 5 weeks. After this animals were killed and tumors excised and weighed. (*): statistically significance according to the non-parametric Kruskal Wallis test.
Figure 4:
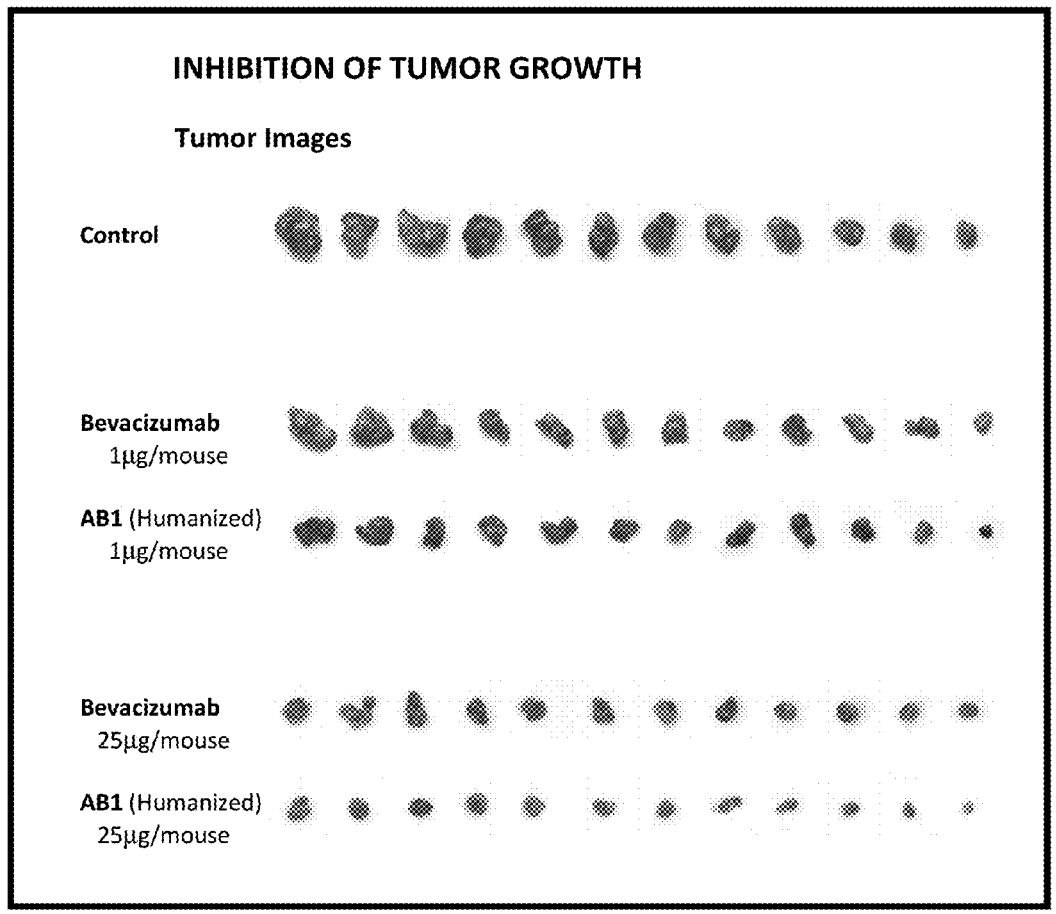
FIG. 4 depicts tumor images illustrating the inhibition of IIB-Mel-J tumor growth in nude mice as a function of the dose of the humanized version of the mouse mMcA-AB1-anti-VEGF-A monoclonal antibody of this invention or the anti-VEGF monoclonal antibody Bevacizumab (AVASTIN™).
Figure 5:
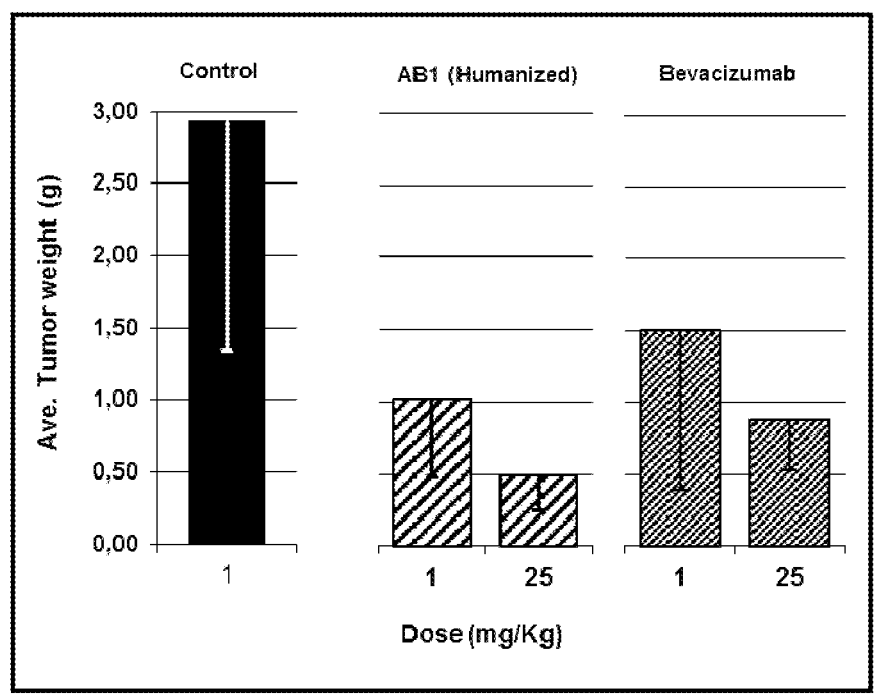
FIG. 5 depicts inhibition of IIB-Mel-J tumor growth in nude mice after treatment with the humanized version of the mouse mMcA-AB1-anti-VEGF-A monoclonal antibody of this invention or Bevacizumab (AVASTIN™) at the following doses: 1 μg/mouse or 25 μg/mouse, twice a week for 5 weeks. After this animals were killed and tumors excised and weighed. (*): statistically significance to the control according to the non-parametric Kruskal Wallis test. (**): statistically significance to the Bevacizumab treatment according to the non-parametric Kruskal Wallis test.

Animals were killed at day 40 and tumors excised and weighed. The results show that there was a significant inhibition of tumor growth when both, AB1 and the humanized version of AB1 antibodies were administered in all the assayed doses to mice in comparison with mice injected with PBS (p<0.001) (FIG. 3). On the other hand, tumors of animals treated with the AB1 and humanized AB1 antibodies were, after 40 days of treatment, in average smaller than tumors treated with Bevacizumab at both of the assayed doses (FIG. 4). Comparison between the humanized version of AB1 and Bevacizumab are shown in FIG. 5. At the 25 µg/mouse differences between these two antibodies were statistically significant (p<0.001). It is worth mention that all the assayed antibodies lack significant neutralizing activity to mouse VEGF (Liang W, Wu X, Peale F V et al. Cross-species Vascular Endothelial Growth factor (VEGF)-blocking Antibodies Completely Inhibit the Growth of Human Tumor Xenografts and Measure the Contribution of Stromal VEGF. JBC 281: 951-961 (2006) and EXAMPLE 1) a fact that renders comparison between its anti-tumor activities meaningful.

What is claimed is:

1. An isolated antibody or antigen-binding fragment thereof that specifically binds human VEGF-A and VEGF-B and comprises a light chain immunoglobulin comprising CDR1 comprising the amino acid sequence set forth in SEQ ID NO: 10, CDR2 comprising the amino acid sequence set forth in SEQ ID NO: 11 and CDR3 comprising the amino acid sequence set forth in SEQ ID NO: 12 and a heavy chain immunoglobulin comprising CDR1 comprising the amino acid sequence set forth in SEQ ID NO: 7, CDR2 comprising the amino acid sequence set forth in SEQ ID NO: 8 and CDR3 comprising the amino acid sequence set forth in SEQ ID NO: 9.

2. The antibody or antigen-binding fragment thereof as recited in claim 1, comprising a light chain immunoglobulin comprising the amino acid sequence set forth in SEQ ID NO:4; and a heavy chain immunoglobulin comprising the amino acid sequence set forth in SEQ ID NO:3.

3. The antibody or antigen-binding fragment thereof as recited in claim 1, comprising a light chain immunoglobulin comprising the amino acid sequence set forth in SEQ ID NO:6; and a heavy chain immunoglobulin comprising the amino acid sequence set forth in SEQ ID NO:5.

4. The antibody or antigen-binding fragment thereof as recited in claim 1, wherein the antibody or antigen-binding fragment thereof is selected from the group consisting of a monoclonal antibody, a polyclonal antibody, a chimeric antibody, a humanized antibody, a recombinant antibody, a fully human antibody, a bivalent antibody, an anti-idiotypic antibody, a camelized single domain antibody, a diabody, a scFv, an scFv dimer, a dsFv, a (dsFv).sub.2, a dsFv-dsFv', an Fv fragment, a Fab, a Fab', a F(ab').sub.2, a ds diabody, a nanobody, a domain antibody, and a bivalent domain antibody.

5. The antibody or antigen-binding fragment thereof as recited in claim 1, further comprising an immunoglobulin constant region selected from the group consisting of a .kappa. light chain, a .gamma.1 heavy chain, a .gamma.2 heavy chain, a .gamma.3 heavy chain, and a .gamma.4 heavy chain constant region.

6. The antibody or antigen-binding fragment thereof as recited in claim 1, wherein said antibody or antigen-binding fragment inhibits tumor growth in a greater extent than Bevacizumab when administered at the same dosage.

7. The antibody or antigen-binding fragment thereof as recited in claim 1, wherein said antibody or antigen-binding fragment binds human VEGF.sub.165 with a K.sub.D of no more than $10^{-10}$.

8. A pharmaceutical composition comprising the antibody or antigen-binding fragment thereof as recited in claim 1 and one or more antioxidants.

9. The pharmaceutical composition of claim 8, wherein said one or more antioxidants are selected from the group consisting of methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate.

10. A pharmaceutical composition comprising the antibody or antigen-binding fragment thereof as recited in claim 1 and one or more pharmaceutically acceptable carriers.

11. A pharmaceutical composition comprising the antibody or antigen-binding fragment thereof as recited in claim 1 in combination with at least one chemotherapeutic agent selected from the group consisting of capecitabine, a combination of irinotecan, 5-fluorouracil and leucovorin, carboplatin, leucovorin, oxaliplatin, and 5-fluorouracil.

12. A method of inhibiting angiogenesis in a human in need thereof comprising administering to said human a therapeutically effective amount of the antibody or antigen-binding fragment thereof as recited in claim 1, optionally in combination with at least one chemotherapeutic agent.

13. The method according to claim 12, wherein the human has a condition associated with aberrant angiogenesis.

14. The method according to claim 12, wherein the human has an inflammatory disease associated with VEGF signaling.

15. The method according to claim 14 wherein the inflammatory disease is rheumatoid arthritis.

16. The method according to claim 12 wherein the human has wet acute macular degeneration or diabetic retinopathy.

17. The method according to claim 12, wherein the human has a cancer associated with increased VEGF signaling.

18. The method according to claim 17 wherein said cancer is a breast cancer.

* * * * *

SEQUENCE LISTING

```
<160> NUMBER OF SEQ ID NOS: 31

<210> SEQ ID NO 1
<211> LENGTH: 165
<212> TYPE: PRT
<213> ORGANISM: Homo sapiens

<400> SEQUENCE: 1

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160
```

Asp Lys Pro Arg Arg
            165

<210> SEQ ID NO 2
<211> LENGTH: 185
<212> TYPE: PRT
<213> ORGANISM: Homo sapiens

<400> SEQUENCE: 2

Pro Val Ser Gln Pro Asp Ala Pro Gly His Gln Arg Lys Val Val Ser
1               5                   10                  15

Trp Ile Asp Val Tyr Thr Arg Ala Thr Cys Gln Pro Arg Glu Val Val
            20                  25                  30

Val Pro Leu Thr Val Glu Leu Met Gly Thr Val Ala Lys Gln Leu Val
        35                  40                  45

Pro Ser Cys Val Thr Val Gln Arg Cys Gly Gly Cys Cys Pro Asp Asp
    50                  55                  60

Gly Leu Glu Cys Val Pro Thr Gly Gln His Gln Val Arg Met Gln Ile
65                  70                  75                  80

Leu Met Ile Arg Tyr Pro Ser Ser Gln Leu Gly Glu Met Ser Leu Glu
                85                  90                  95

Glu His Ser Gln Cys Glu Cys Arg Pro Lys Lys Lys Asp Ser Ala Val
            100                 105                 110

Lys Pro Asp Arg Ala Ala Thr Pro His His Arg Pro Gln Pro Arg Ser
        115                 120                 125

Val Pro Gly Trp Asp Ser Ala Pro Gly Ala Pro Pro Ala Asp Ile Thr
    130                 135                 140

His Pro Thr Pro Ala Pro Gly Pro Ser Ala His Ala Ala Pro Ser Thr
145                 150                 155                 160

Thr Ser Ala Leu Thr Pro Gly Pro Ala Ala Ala Ala Asp Ala Ala
                165                 170                 175

Ala Ser Ser Val Ala Lys Gly Gly Ala
            180                 185

<210> SEQ ID NO 3
<211> LENGTH: 121
<212> TYPE: PRT
<213> ORGANISM: Mus muculus

<400> SEQUENCE: 3

Gln Val Lys Leu Leu Glu Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Val Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Ser Asn Leu Asn Asn Glu Asp Thr Ala Thr Tyr Phe Cys
                85                  90                  95

Ala Arg Tyr Tyr Gly Ser Thr Ser Val Trp Tyr Phe Asp Val Trp Gly
            100                 105                 110

Ala Gly Thr Thr Val Thr Val Ser Ser
        115                 120

<210> SEQ ID NO 4
<211> LENGTH: 108
<212> TYPE: PRT
<213> ORGANISM: Mus muculus

<400> SEQUENCE: 4

Glu Leu Val Met Thr Gln Thr Pro Ser Ser Leu Ser Ala Ser Leu Gly
1               5                   10                  15

Asp Arg Val Thr Ile Thr Cys Arg Ala Ser Gln Asp Ile Phe Asn Tyr
            20                  25                  30

Leu Asn Trp Tyr Gln Gln Lys Pro Asp Gly Pro Ile Lys Leu Leu Ile
        35                  40                  45

Tyr Tyr Ser Ser Arg Leu His Ser Gly Val Pro Ser Arg Phe Ser Gly
50                  55                  60

Ser Gly Ser Gly Thr Asp Tyr Ser Leu Thr Ile Ser Asn Leu Asp Arg
65                  70                  75                  80

Glu Asp Ile Ala Thr Tyr Phe Cys Gln Gln Gly Phe Thr Leu Pro Trp
                85                  90                  95

Thr Phe Gly Gly Gly Thr Lys Leu Glu Ile Lys Arg
            100                 105

<210> SEQ ID NO 5
<211> LENGTH: 121
<212> TYPE: PRT
<213> ORGANISM: Artificial sequence
<220> FEATURE:
<223> OTHER INFORMATION: recombinant anti-VEGF antibody light variable
      region

<400> SEQUENCE: 5

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Val Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Tyr Gly Ser Thr Ser Val Trp Tyr Phe Asp Val Trp Gly
            100                 105                 110

Arg Gly Thr Leu Val Thr Val Ser Ser
        115                 120

<210> SEQ ID NO 6
<211> LENGTH: 108
<212> TYPE: PRT
<213> ORGANISM: Artificial sequence
<220> FEATURE:
<223> OTHER INFORMATION: recombinant anti-VEGF antibody light variable
      region

<400> SEQUENCE: 6

Asp Ile Gln Met Thr Gln Ser Pro Ser Ser Leu Ser Ala Ser Val Gly
1               5                   10                  15

-continued

Asp Arg Val Thr Ile Thr Cys Arg Ala Ser Gln Asp Ile Phe Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Phe Thr Leu Pro Trp
                85                  90                  95

Thr Phe Gly Gln Gly Thr Lys Val Glu Ile Lys Arg
            100                 105

<210> SEQ ID NO 7
<211> LENGTH: 10
<212> TYPE: PRT
<213> ORGANISM: Mus muculus

<400> SEQUENCE: 7

Gly Tyr Thr Phe Thr Asn Phe Gly Met Asn
1               5                   10

<210> SEQ ID NO 8
<211> LENGTH: 17
<212> TYPE: PRT
<213> ORGANISM: Mus muculus

<400> SEQUENCE: 8

Trp Ile Asn Thr Asn Thr Gly Glu Pro Thr Tyr Val Asp Asp Phe Lys
1               5                   10                  15

Gly

<210> SEQ ID NO 9
<211> LENGTH: 12
<212> TYPE: PRT
<213> ORGANISM: Mus muculus

<400> SEQUENCE: 9

Tyr Tyr Gly Ser Thr Ser Val Trp Tyr Phe Asp Val
1               5                   10

<210> SEQ ID NO 10
<211> LENGTH: 11
<212> TYPE: PRT
<213> ORGANISM: Mus muculus

<400> SEQUENCE: 10

Arg Ala Ser Gln Asp Ile Phe Asn Tyr Leu Asn
1               5                   10

<210> SEQ ID NO 11
<211> LENGTH: 6
<212> TYPE: PRT
<213> ORGANISM: Mus muculus

<400> SEQUENCE: 11

Tyr Ser Ser Arg Leu His
1               5

<210> SEQ ID NO 12
<211> LENGTH: 9
<212> TYPE: PRT

```
<213> ORGANISM: Mus muculus

<400> SEQUENCE: 12

Gln Gln Gly Phe Thr Leu Pro Trp Thr
1               5

<210> SEQ ID NO 13
<211> LENGTH: 17
<212> TYPE: PRT
<213> ORGANISM: Homo sapiens

<400> SEQUENCE: 13

His His Glu Val Val Lys Phe Met Asp Val Tyr Gln Arg Ser Tyr Cys
1               5                   10                  15

His

<210> SEQ ID NO 14
<211> LENGTH: 12
<212> TYPE: PRT
<213> ORGANISM: Homo sapiens

<400> SEQUENCE: 14

Tyr Ile Phe Lys Pro Ser Cys Val Pro Leu Met Arg
1               5                   10

<210> SEQ ID NO 15
<211> LENGTH: 14
<212> TYPE: PRT
<213> ORGANISM: Homo sapiens

<400> SEQUENCE: 15

Gln Ile Met Arg Ile Lys Pro His Gln Gly Gln His Ile Gly
1               5                   10

<210> SEQ ID NO 16
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 16
aggtccagct gctcgagtct gg                                              22

<210> SEQ ID NO 17
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 17
aggtccagct gctcgagtct gg                                              22

<210> SEQ ID NO 18
<211> LENGTH: 22
<212> TYPE: DNA
<213> ORGANISM: Artificial sequence
<220> FEATURE:
<223> OTHER INFORMATION: primer for amplification of the DNA sequences
      codifying the variable heavy chain of a mouse antibody

<400> SEQUENCE: 18
```
aggtccagct gctcgagtca gg                                                    22

<210> SEQ ID NO 19
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 19
aggtccagct tctcgagtct gg                                                    22

<210> SEQ ID NO 20
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 20
aggtccagct tctcgagtca gg                                                    22

<210> SEQ ID NO 21
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 21
aggtccaact gctcgagtct gg                                                    22

<210> SEQ ID NO 22
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 22
aggtccaact gctcgagtca gg                                                    22

<210> SEQ ID NO 23
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 23
aggtccaact tctcgagtct gg                                                    22

<210> SEQ ID NO 24
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 24
aggtccaact tctcgagtca gg                                                    22

<210> SEQ ID NO 25
<211> LENGTH: 22
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 25
aggtcgaact tctcgagtct gg                                              22

<210> SEQ ID NO 26
<211> LENGTH: 32
<212> TYPE: DNA
<213> ORGANISM: Artificial sequence
<220> FEATURE:
<223> OTHER INFORMATION: primer for amplification of the DNA sequence
      codifying the variable heavy chain of a mouse antibody

<400> SEQUENCE: 26
aggctttact agtacaatcc ctgggcacaa tt                                   32

<210> SEQ ID NO 27
<211> LENGTH: 32
<212> TYPE: DNA
<213> ORGANISM: Artificial sequence
<220> FEATURE:
<223> OTHER INFORMATION: primer for amplification of the DNA sequence
      codifying the variable light chain of a mouse antibody

<400> SEQUENCE: 27
ccagttccga gctcgtgctc acccagtctc ca                                   32

<210> SEQ ID NO 28
<211> LENGTH: 32
<212> TYPE: DNA
<213> ORGANISM: Artificial sequence
<220> FEATURE:
<223> OTHER INFORMATION: primer for amplification of the DNA sequence
      codifying the variable light chain of a mouse antibody

<400> SEQUENCE: 28
ccagttccga gctccagatg acccagtctc ca                                   32

<210> SEQ ID NO 29
<211> LENGTH: 32
<212> TYPE: DNA
<213> ORGANISM: Artificial sequence
<220> FEATURE:
<223> OTHER INFORMATION: primer for amplification of the DNA sequence
      codifying the variable light chain of a mouse antibody

<400> SEQUENCE: 29
ccagatgtga gctcgtgatg acccagactc ca                                   32

<210> SEQ ID NO 30
<211> LENGTH: 32
<212> TYPE: DNA
<213> ORGANISM: Artificial sequence
<220> FEATURE:
<223> OTHER INFORMATION: primer for amplification of the DNA sequence
      codifying the variable light chain of a mouse antibody

<400> SEQUENCE: 30
ccagatgtga gctcgtcatg acccagtctc ca                                   32

```
<210> SEQ ID NO 31
<211> LENGTH: 34
<212> TYPE: DNA
<213> ORGANISM: Artificial sequence
<220> FEATURE:
<223> OTHER INFORMATION: primer for amplification of the DNA sequence
      codifying the variable light chain of a mouse antibody

<400> SEQUENCE: 31
gcgccgtcta gaattaacac tcattcctgt tgaa                                34
```